(12) United States Patent
Zacharias

(10) Patent No.: US 8,579,969 B2
(45) Date of Patent: Nov. 12, 2013

(54) DUAL MODE AUTOMATED INTRAOCULAR LENS INJECTOR DEVICE

(75) Inventor: Jaime Zacharias, Santiago (CL)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 13/188,498

(22) Filed: Jul. 22, 2011

(65) Prior Publication Data
US 2012/0022548 A1  Jan. 26, 2012

Related U.S. Application Data

(60) Provisional application No. 61/367,440, filed on Jul. 25, 2010.

(51) Int. Cl.
A61F 2/16 (2006.01)
(52) U.S. Cl.
USPC .......................................... 623/6.12; 606/107
(58) Field of Classification Search
USPC .............................. 606/107; 623/6.12; 604/22
See application file for complete search history.

(56) References Cited

U.S. PATENT DOCUMENTS

| 4,573,998 | A |  | 3/1986 | Mazzocco |
|---|---|---|---|---|
| 4,619,657 | A |  | 10/1986 | Keates et al. |
| 4,627,835 | A | * | 12/1986 | Fenton, Jr. .................. 604/67 |
| 4,681,102 | A |  | 7/1987 | Bartell |
| 4,747,404 | A |  | 5/1988 | Jampel et al. |
| 4,834,094 | A |  | 5/1989 | Patton et al. |
| 4,836,201 | A |  | 6/1989 | Patton et al. |
| 4,919,130 | A |  | 4/1990 | Stoy et al. |
| 4,934,363 | A |  | 6/1990 | Smith et al. |
| 4,960,557 | A |  | 10/1990 | Sorensen |
| 5,007,913 | A |  | 4/1991 | Dulebohn et al. |
| 5,026,396 | A |  | 6/1991 | Darin |
| 5,098,439 | A |  | 3/1992 | Hill et al. |
| 5,190,552 | A |  | 3/1993 | Kelman |
| 5,275,604 | A |  | 1/1994 | Rheinish et al. |
| 5,304,182 | A |  | 4/1994 | Rheinish et al. |
| 5,354,333 | A |  | 10/1994 | Kammann et al. |

(Continued)

FOREIGN PATENT DOCUMENTS

| AU | 728443 | 1/2001 |
|---|---|---|
| DE | 4133402 C1 | 1/1993 |

(Continued)

OTHER PUBLICATIONS

International Searching Authority, International Search Report, PCT/US2011/044917, Oct. 27, 2011, 5 pages.

(Continued)

*Primary Examiner* — Ryan Severson
*Assistant Examiner* — Katherine M Shi
(74) *Attorney, Agent, or Firm* — Kenneth Bassinger

(57) ABSTRACT

An IOL injector device allows for both powered and manual delivery of an IOL. The injector has a tubular housing. A plunger is longitudinally disposed within the housing and has first and second ends. The first end is disposed towards the front end of the housing. A drive system is coupled to the housing. The drive system causes longitudinal translation of the plunger along the primary axis of the housing. A normally engaged clutch system is coupled to the drive system. The normally engaged clutch system allows manual disengagement of the drive system. A knob coupled to the plunger allows for manual operation of the injector.

14 Claims, 10 Drawing Sheets

(56) References Cited

U.S. PATENT DOCUMENTS

| | | | |
|---|---|---|---|
| 5,397,313 | A | 3/1995 | Gross |
| 5,425,734 | A | 6/1995 | Blake |
| 5,444,183 | A | 8/1995 | Gehrs et al. |
| 5,464,396 | A | 11/1995 | Barta et al. |
| 5,468,246 | A | 11/1995 | Blake |
| 5,494,484 | A | 2/1996 | Feingold |
| 5,496,278 | A | 3/1996 | Buff |
| 5,496,328 | A | 3/1996 | Nakajima et al. |
| 5,499,987 | A | 3/1996 | Feingold |
| 5,578,042 | A | 11/1996 | Cumming |
| 5,582,614 | A | 12/1996 | Feingold |
| 5,607,433 | A | 3/1997 | Polla et al. |
| 5,616,148 | A | 4/1997 | Eagles et al. |
| 5,620,450 | A | 4/1997 | Eagles et al. |
| 5,629,577 | A | 5/1997 | Polla et al. |
| 5,643,275 | A | 7/1997 | Blake |
| 5,643,276 | A | 7/1997 | Zaleski |
| 5,653,715 | A | 8/1997 | Reich et al. |
| 5,653,753 | A | 8/1997 | Brady et al. |
| 5,716,364 | A | 2/1998 | Makker et al. |
| 5,728,102 | A | 3/1998 | Feingold et al. |
| 5,735,858 | A | 4/1998 | Makker et al. |
| 5,772,666 | A | 6/1998 | Feingold et al. |
| 5,776,138 | A | 7/1998 | Vidal et al. |
| 5,800,441 | A | 9/1998 | Polla et al. |
| 5,800,442 | A | 9/1998 | Wolf et al. |
| 5,803,925 | A | 9/1998 | Yang et al. |
| 5,810,834 | A | 9/1998 | Heyman |
| 5,820,373 | A | 10/1998 | Okano et al. |
| 5,860,986 | A | 1/1999 | Reich et al. |
| 5,868,752 | A | 2/1999 | Makker et al. |
| 5,873,879 | A | 2/1999 | Figueroa et al. |
| 5,876,406 | A | 3/1999 | Wolf et al. |
| 5,876,407 | A | 3/1999 | Makker et al. |
| 5,891,153 | A | 4/1999 | Peterson |
| 5,928,245 | A | 7/1999 | Wolf et al. |
| 5,944,725 | A | 8/1999 | Cicenas et al. |
| 5,947,976 | A | 9/1999 | Van Noy et al. |
| 6,010,510 | A | 1/2000 | Brown et al. |
| 6,042,587 | A | 3/2000 | Polla et al. |
| 6,056,758 | A | 5/2000 | Vidal et al. |
| 6,083,231 | A | 7/2000 | Van Noy et al. |
| 6,140,602 | A | 10/2000 | Costin |
| 6,143,001 | A | 11/2000 | Brown et al. |
| 6,162,229 | A | 12/2000 | Feingold et al. |
| 6,162,230 | A | 12/2000 | Polla et al. |
| 6,179,843 | B1 | 1/2001 | Weiler |
| 6,228,094 | B1 | 5/2001 | Erdman |
| 6,241,737 | B1 | 6/2001 | Feingold |
| 6,254,607 | B1 | 7/2001 | Makker et al. |
| 6,312,433 | B1 | 11/2001 | Butts et al. |
| 6,334,862 | B1 | 1/2002 | Vidal et al. |
| 6,355,046 | B2 | 3/2002 | Kikuchi et al. |
| 6,387,101 | B1 | 5/2002 | Butts et al. |
| 6,398,789 | B1 | 6/2002 | Capetan |
| 6,406,481 | B2 | 6/2002 | Feingold et al. |
| 6,423,035 | B1 | 7/2002 | Das et al. |
| 6,447,519 | B1 | 9/2002 | Brady et al. |
| 6,468,282 | B2 | 10/2002 | Kikuchi et al. |
| 6,471,708 | B2 | 10/2002 | Green |
| 6,491,697 | B1 | 12/2002 | Clark et al. |
| 6,497,708 | B1 | 12/2002 | Cumming |
| 6,500,181 | B1 | 12/2002 | Portney |
| 6,503,275 | B1 | 1/2003 | Cumming |
| 6,506,195 | B2 | 1/2003 | Chambers et al. |
| 6,558,395 | B2 | 5/2003 | Hjertman et al. |
| 6,592,591 | B2 | 7/2003 | Polla et al. |
| 6,607,537 | B1 | 8/2003 | Binder |
| 6,635,731 | B2 | 10/2003 | Mentak |
| 6,666,871 | B2 | 12/2003 | Kikuchi et al. |
| 6,685,740 | B2 | 2/2004 | Figueroa et al. |
| 6,899,717 | B2 | 5/2005 | Weber et al. |
| 6,923,815 | B2 | 8/2005 | Brady et al. |
| 6,964,648 | B2 | 11/2005 | Talling et al. |
| 6,976,989 | B1 | 12/2005 | Vincent |
| 7,014,641 | B2 | 3/2006 | Kobayashi et al. |
| 7,042,180 | B2 | 5/2006 | Terry et al. |
| 7,131,976 | B2 | 11/2006 | Kobayashi et al. |
| 7,156,854 | B2 | 1/2007 | Brown et al. |
| 7,156,855 | B2 | 1/2007 | Oda |
| 7,189,218 | B2 | 3/2007 | Lichtenberg |
| 7,279,006 | B2 | 10/2007 | Vincent |
| 7,422,604 | B2 | 9/2008 | Vaquero et al. |
| 7,429,263 | B2 | 9/2008 | Vaquero et al. |
| 2001/0007075 | A1* | 7/2001 | Hjertman et al. ............ 606/107 |
| 2002/0151904 | A1 | 10/2002 | Feingold et al. |
| 2003/0040755 | A1 | 2/2003 | Meyer |
| 2003/0135221 | A1 | 7/2003 | Sabet |
| 2003/0139749 | A1 | 7/2003 | Kikuchi et al. |
| 2003/0212406 | A1 | 11/2003 | Kobayashi et al. |
| 2003/0212409 | A1 | 11/2003 | Kobayashi et al. |
| 2004/0054374 | A1 | 3/2004 | Weber et al. |
| 2004/0087896 | A1 | 5/2004 | Wise et al. |
| 2004/0097956 | A1 | 5/2004 | Oda |
| 2004/0147938 | A1 | 7/2004 | Dusek et al. |
| 2004/0160575 | A1 | 8/2004 | Ayton et al. |
| 2004/0199174 | A1 | 10/2004 | Herberger et al. |
| 2004/0215207 | A1 | 10/2004 | Cumming |
| 2004/0238392 | A1 | 12/2004 | Peterson et al. |
| 2005/0049605 | A1 | 3/2005 | Vaquero et al. |
| 2005/0049606 | A1 | 3/2005 | Vaquero et al. |
| 2005/0065534 | A1 | 3/2005 | Hohl |
| 2005/0143750 | A1 | 6/2005 | Vaquero |
| 2005/0149056 | A1 | 7/2005 | Rathert |
| 2005/0149057 | A1 | 7/2005 | Rathert |
| 2005/0203619 | A1 | 9/2005 | Altmann |
| 2005/0222578 | A1 | 10/2005 | Vaquero |
| 2005/0222579 | A1 | 10/2005 | Vaquero et al. |
| 2006/0066962 | A1 | 3/2006 | Totzeck et al. |
| 2006/0085013 | A1 | 4/2006 | Dusek et al. |
| 2006/0167466 | A1 | 7/2006 | Dusek |
| 2006/0184181 | A1 | 8/2006 | Cole et al. |
| 2006/0200167 | A1 | 9/2006 | Peterson et al. |
| 2006/0229633 | A1 | 10/2006 | Shepherd |
| 2006/0229634 | A1 | 10/2006 | Shepherd |
| 2006/0235429 | A1 | 10/2006 | Lee et al. |
| 2006/0284581 | A1 | 12/2006 | Mullin et al. |
| 2007/0005135 | A1 | 1/2007 | Makker et al. |
| 2007/0050023 | A1 | 3/2007 | Bessiere et al. |
| 2007/0060925 | A1 | 3/2007 | Pynson |
| 2007/0150056 | A1 | 6/2007 | Meyer |
| 2007/0173860 | A1 | 7/2007 | Iwaski |
| 2008/0033449 | A1 | 2/2008 | Cole et al. |
| 2008/0039862 | A1 | 2/2008 | Tran |
| 2008/0058830 | A1 | 3/2008 | Cole et al. |
| 2008/0097459 | A1 | 4/2008 | Kammerlander et al. |
| 2008/0119865 | A1 | 5/2008 | Meunier et al. |
| 2008/0200920 | A1 | 8/2008 | Downer |
| 2008/0200921 | A1 | 8/2008 | Downer |
| 2008/0221584 | A1 | 9/2008 | Downer |
| 2008/0221585 | A1 | 9/2008 | Downer |
| 2008/0255577 | A1 | 10/2008 | Downer |
| 2009/0043313 | A1 | 2/2009 | Ichinohe et al. |
| 2009/0112223 | A1 | 4/2009 | Downer |
| 2009/0171366 | A1 | 7/2009 | Tanaka |
| 2009/0204123 | A1 | 8/2009 | Downer |
| 2009/0216244 | A1 | 8/2009 | Pynson |
| 2009/0264940 | A1* | 10/2009 | Beale et al. ................. 606/86 R |
| 2010/0049090 | A1* | 2/2010 | Konya et al. ................. 600/583 |
| 2010/0094309 | A1 | 4/2010 | Boukhny et al. |
| 2010/0204704 | A1* | 8/2010 | Davies et al. ................ 606/107 |

FOREIGN PATENT DOCUMENTS

| | | |
|---|---|---|
| DE | 4301573 | 7/1994 |
| EP | 0174917 | 3/1986 |
| EP | 0 270257 | 6/1988 |
| EP | 0 363 213 | 4/1990 |
| EP | 0477466 | 6/1996 |
| EP | 0 858 304 | 8/1998 |
| EP | 0962195 | 12/1999 |
| EP | 1011561 | 6/2000 |
| EP | 1076408 | 2/2001 |
| EP | 1322731 B1 | 8/2003 |

(56) References Cited

FOREIGN PATENT DOCUMENTS

| | | |
|---|---|---|
| EP | 1332731 A1 | 8/2003 |
| EP | 1360944 A2 | 11/2003 |
| EP | 1481652 | 12/2004 |
| EP | 1661533 | 5/2006 |
| EP | 1849436 A1 | 10/2007 |
| EP | 1891911 | 2/2008 |
| EP | 1958593 | 8/2008 |
| EP | 1958594 | 8/2008 |
| EP | 2062552 | 5/2009 |
| EP | 2085053 | 8/2009 |
| FR | 2820633 | 8/2002 |
| GB | 2224214 | 5/1990 |
| JP | 1176288 | 12/1989 |
| JP | 10309294 | 11/1998 |
| JP | 10511876 | 11/1998 |
| JP | 10512460 | 11/1998 |
| JP | 20000025073 | 1/2000 |
| JP | 2003070829 | 3/2003 |
| JP | 2003325569 | 11/2003 |
| JP | 2006014962 | 1/2006 |
| JP | 2006181269 | 7/2006 |
| JP | 2007055057 | 3/2007 |
| RU | 2138232 | 9/1999 |
| RU | 2171100 | 7/2001 |
| RU | 2238283 | 10/2004 |
| RU | 2242956 | 12/2004 |
| SU | 1440496 | 11/1988 |
| WO | WO 94/07436 | 4/1994 |
| WO | WO 94/20027 | 9/1994 |
| WO | WO 96/10372 | 4/1996 |
| WO | WO 96/20662 | 7/1996 |
| WO | WO 96/28122 | 9/1996 |
| WO | WO 96/28122 A1 | 9/1996 |
| WO | WO 96/29956 | 10/1996 |
| WO | WO 97/15253 | 5/1997 |
| WO | WO 97/26841 | 7/1997 |
| WO | WO 98/52581 | 2/1998 |
| WO | WO 98/12969 | 4/1998 |
| WO | WO 98/15244 | 4/1998 |
| WO | WO 98/20819 | 5/1998 |
| WO | WO 00/40175 | 7/2000 |
| WO | WO 00/62712 | 10/2000 |
| WO | WO 02/060338 A2 | 8/2002 |
| WO | WO 2004/091447 | 10/2004 |
| WO | WO 2005/018515 | 3/2005 |
| WO | WO 2005/020853 | 3/2005 |
| WO | WO 2005/023154 A2 | 3/2005 |
| WO | WO 2005/023154 A3 | 3/2005 |
| WO | WO 2005/102223 | 11/2005 |
| WO | WO 2006/059183 | 6/2006 |
| WO | WO 2006/070561 | 7/2006 |
| WO | WO 2006/080191 | 8/2006 |
| WO | WO 2006/113138 | 10/2006 |
| WO | WO 2006/113357 | 10/2006 |
| WO | WO 2007/080868 | 7/2007 |

OTHER PUBLICATIONS

International Searching Authority, Written Opinion of the International Searching Authority, PCT/US2011/044917, Oct. 27, 2011, 6 pages.
International Search Report for PCT/US2009/057,083, Filed Sep. 16, 2009, Publication No. WO2010/044,974, Published Apr. 22, 2010, 5 pages.
Written Opinion of the International Searching Authority, International Application No. PCT/US2009/057,083, Filed Sep. 16, 2009, Publication No. WO2010/044,974, Published Apr. 22, 2010, 6 pages.
Abstract of article entitled "Implantation of the AcrySof MA30BA lens using the Monarch System" by Barakova D., original article found in Cesk slov Oftalmol, 2002 58(3), at p. 149-152, found in PubMed database at http://www.ncbi.nlm.nih.gov/pubmed/12087658 (1 page).
International Preliminary Report on Patentability with Written Opinion, dated Apr. 19, 2011, Application No. PCT/US2009/057083, Filed Sep. 16, 2009, Publication No. WO2010/044,974, Published Apr. 22, 2010, 7 pages.
European Search Report for Application No. 08102172.7, Publication No. 1980219, dated Oct. 15, 2008, 5 pages.
International Search Report for PCT/US2009/067814, Publication No. WO2010/080351, 5 pages.

* cited by examiner

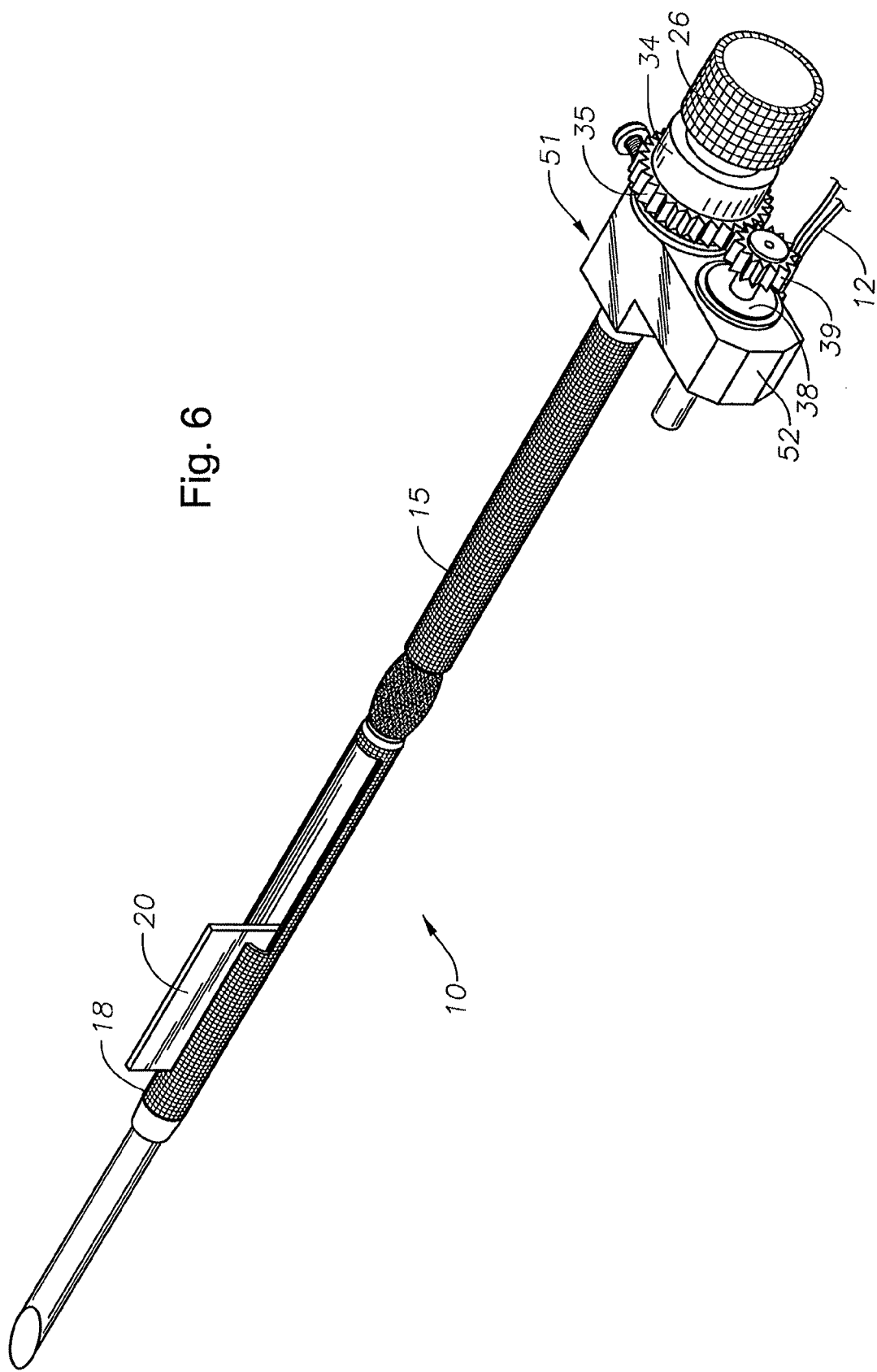

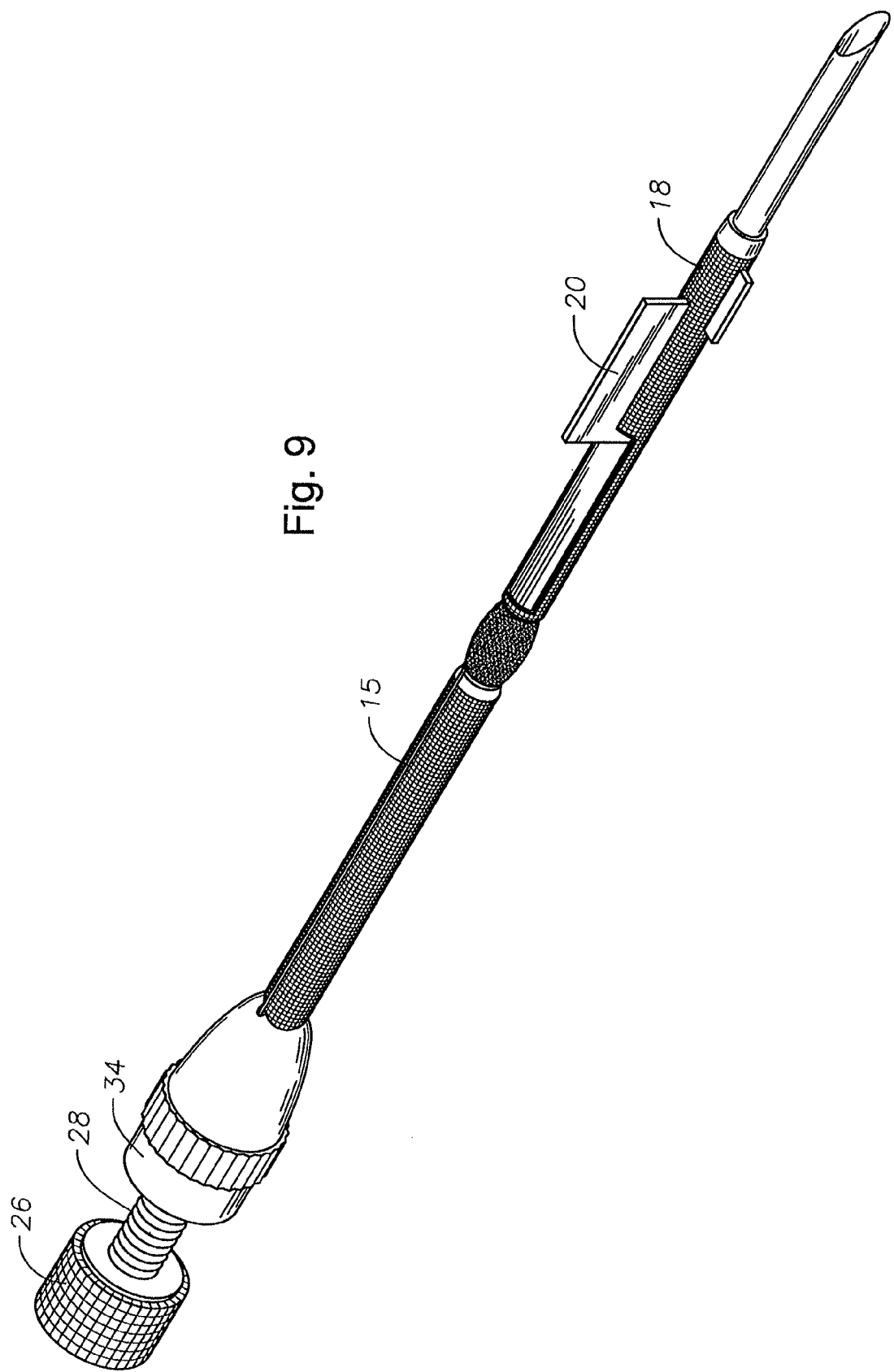

DUAL MODE AUTOMATED INTRAOCULAR LENS INJECTOR DEVICE

This application claims the benefit of U.S. Provisional Patent Application No. 61/367,440 filed Jul. 25, 2010.

BACKGROUND OF THE INVENTION

The present invention relates generally to a device for delivering an intraocular lens into an eye. The device has both a powered modality of operation and a manual modality of operation. The manual modality of operation may at any time override the powered modality of operation while providing the same accuracy and safety of known manual threaded lens delivering devices.

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

The IOL is injected into the eye through the same small incision used to remove the diseased lens. An insertion cartridge of an IOL injector is loaded with the IOL, the tip of the insertion cartridge is inserted into the incision, and the lens is delivered into the eye.

Many IOLs manufactured today are made from a polymer with specific characteristics. These characteristics allow the lens to be folded, and when delivered into the eye, allow the lens to unfold into the proper shape. Several manual injector devices are available for implanting these lenses into the eye. However, threaded-type manual injectors require the use of two hands, which is cumbersome and tedious. Syringe-type injectors produce inconsistent injection force and displacement. Thus, improved devices and methods are needed for delivering IOLs into the eye.

SUMMARY OF THE INVENTION

Various embodiments of the present invention provide an intraocular lens injector that can operate in dual mode—capable of motor powered operation and manual operation. Automated and manual modes of operation can occur at any time of lens insertion, the manual mode preferably overriding the automated mode of operation.

The injector of present invention may incorporate a detachable powering mechanism, always being able to operate in manual modality regardless of the availability of the powering module.

The injector of the present invention is may incorporate a mechanical clutching or motor detaching mechanism. Because of the mechanical nature of the clutching system acting as a safety clutch, a variety of powering motors can be used such as spring motor, pneumatic motor, electric motor, and others.

Embodiments of the present invention include various devices for implanting an intraocular lens (IOL) into a selected position inside an eye, as well as methods for controlling such a device. According to an exemplary embodiment, an IOL injection device comprises a tubular housing with a plunger longitudinally disposed within the tubular housing. The plunger is longitudinally translated frontwards and rearwards, with respect to a front end of the housing, by a drive system disposed within or detachably coupled to the housing and comprising a motor. In a preferred embodiment an electric motor is used, but the drive system can incorporate other driving mechanisms such as a spring motor, a pneumatic motor, etc. with corresponding control system. The drive system is effectively coupled to transmit kinetic energy to a lens injecting plunger.

The device is configured so that when the plunger is translated towards the front of the device, its tip engages an intraocular lens insertion cartridge mounted at or near the front end of the housing. The plunger tip, which may in some embodiments be a removable plastic sleeve that snap fits to a push rod, passes through the insertion cartridge to fold and displace an intraocular lens disposed within, and to inject the folded lens into the selected location inside an eye.

In an embodiment incorporating an electric motor as the drive mechanism, the IOL injection device further comprises a control circuit, electrically connected to the electric motor and configured to start translation of the plunger, responsive to user input. The motor is coupled to the plunger by means of a clutching mechanism in normally engaged condition. In normal powered operation, the motor transmits mechanical power across the engaged clutching mechanism to the plunger producing forward or rearward displacement of the plunger body. If increased resistance to plunger displacement occurs, an increase in torque occurs at clutch disk level. The clutch mechanism is factory set to disengage or slide above torque levels considered safe for operation. Optionally a user can adjust the torque required for the clutch mechanism to slide or disengage. The clutching mechanism can also incorporate two different engage-disengage preset threshold torque levels one for forward and another for rearward plunger directions.

A lever or command can be effective to mechanically disengage the powering drive mechanism from the lens injecting plunger, removing in this way the resistance required to manually slide the clutching mechanism. This action restores the normal feedback of resistance provided to the fingers of the operator when using the injector in manual mode of operation.

An overrunning clutch or freewheel mechanism can be incorporated to the injector power transmission mechanism allowing manual override of the powered drive mechanism with minimal increase in injection resistance when operating in the direction of injection, providing enhanced tactile resistance feedback during manually assisted lens injection. With this mechanism, the driving motor always becomes engaged in backward operation and manual drive is always required to retract the plunger, typically requiring disengagement of a torque limiter for plunger retraction.

When using selected powering motors such as those known as "direct drive" without a gearbox, there is no need for a disengage mechanism for manual operation, as the resistance added to manually activate the unpowered motor is negligible. However, the absence of a mechanical clutching mechanism imposes the need of an electronic fault detection system to detect increased resistance during operation.

The motor controller can incorporate rotational speed control and monitoring. The control circuit can monitor the rotational speed of the electric motor, based on the counter-electromotive force, and can detect fault conditions, such as no-load, excessive load, clutch sliding, end-of-forward travel and end-of-rearward travel. The control circuit can operate the motor in ramp mode, progressively increasing plunger speed when started, and resetting the initial speed every time injection is stopped and restarted.

In an exemplary method for controlling a device for implanting an intraocular lens in the lens capsule of an eye, wherein the device comprises a plunger longitudinally disposed inside a tubular housing and an electric drive system including an electric motor and configured to cause longitudinal translation of the plunger along a primary axis of the housing, longitudinal translation of the plunger is initiated responsive to user input. As a safety feature, translation of the plunger is stopped when and if the normally engaged clutch mechanism disengages reactive to an increased resistance to plunger displacement acting as a programmed torque limiter.

Conditions that trigger clutch disengagement may include excessive resistance to forward translation of the plunger and excessive resistance to rearward translation of the plunger. Increased resistance for plunger displacement converts into increased torque at clutch level. If the preset disengagement level is surpassed the clutch stops transmitting motor power to the plunger acting as a safety clutch. Preset disengagement torque levels can be set by design different for forward and for rearward plunger motion. Regardless of the clutch being engaged or disengaged, the injector can always be operated manually in the conventional manner known for manual IOL injectors.

The powering mechanism can be detachably coupled to the injector body in a way that when coupled motor power can be effectively transmitted to the plunger to operate both in powered and manual mode, but also allowing the injector to operate in manual-only modality when the powering mechanism is detached.

In one embodiment of the present invention, an intraocular lens injector comprises: a tubular housing having a primary axis extending between a front end and a rear end of the housing; a plunger longitudinally disposed within the housing and having first and second ends, the first end being disposed towards the front end of the tubular housing; a drive system coupled to the housing, the drive system configured to cause longitudinal translation of the plunger along the primary axis of the housing; a normally engaged clutch system coupled to the drive system, the normally engaged clutch system allowing manual disengagement of the drive system; and a knob coupled to the plunger, the knob allowing manual operation of the injector.

Of course, those skilled in the art will appreciate that the present invention is not limited to the above features, advantages, contexts or examples, and will recognize additional features and advantages upon reading the following detailed description and upon viewing the accompanying drawings.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 6 is a perspective view of a dual mode IOL injection device according to the principles of the present invention.

FIG. 9 is a perspective view of a spring powered embodiment of a dual mode injector according to the principles of the present invention.

DETAILED DESCRIPTION

Reference is now made in detail to the exemplary embodiments of the invention, examples of which are illustrated in the accompanying drawings. Wherever possible, the same reference numbers are used throughout the drawings to refer to the same or like parts.

Figure 1:
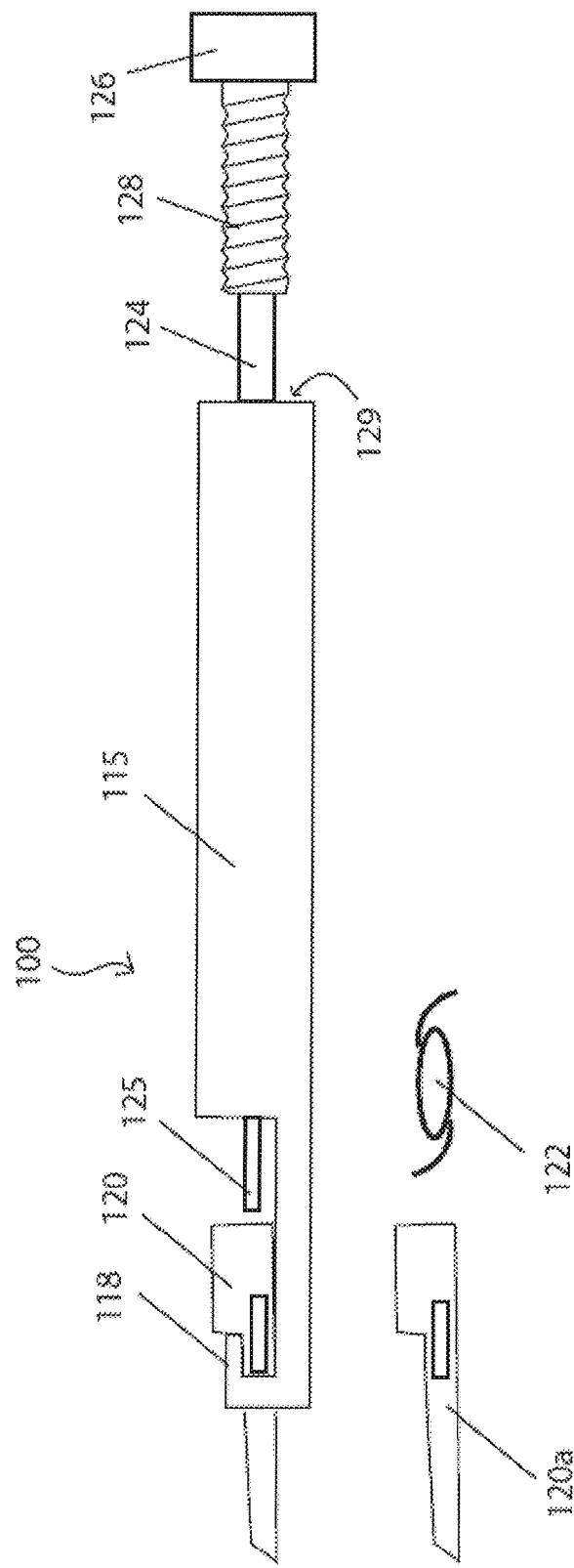
FIG. 1 is a side view of a manually operated IOL injection apparatus of the prior art.

FIG. 1 illustrates a handheld intraocular lens (IOL) injection device of the prior art 100 for implanting an IOL into the anterior capsule of the eye. The IOL injection device 100 also comprises a cartridge mount 118, which holds a removably mounted insertion cartridge 120 typically press fitted into position. Injection cartridge 120 is usually a disposable polymeric component adapted to accommodate an unfolded IOL lens 122 and to fold and displace the lens as a plunger tip 125 is translated forward from a body 115 of injector 100 and through the insertion cartridge 120.

An operator counter rotates a knob 126 until a male thread 128 is released from a receiving female thread 129 fixedly disposed inside injector housing 115. Once thread 128 is released, the operator further pulls backward to retract plunger 124 to its rearward stop position. With plunger 124 in this position, operator can then insert IOL cartridge 120 into its locking position in cartridge mount 118 with IOL 122 properly loaded inside cartridge 120. Some cartridges 120 may come with IOL 122 pre-loaded from factory. The operator pushes knob 126 axially displacing plunger 124 until thread 128 engages female thread 129. At this point IOL 122 will have been pushed by plunger tip 125 inside cartridge 120 into a pre-delivery position. The distal opening of cartridge 120 is inserted into a surgical wound and knob 126 is rotated clockwise to controllably deliver IOL 122 in a desired intraocular location. Injector 100 (with locked cartridge 120) is removed from the eye completing the IOL injection procedure. Tactile feedback allows the operator to sense the force required to advance IOL 122 though the lumen of cartridge 120, thus allowing the operator to detect abnormal situations such as increased resistance (that may be created by a number of conditions such as improper lubrication, misaligned IOL, improper matching between cartridge 120 and IOL 122 dimensions, etc). The operator can evaluate the nature of the condition and perform the corrective actions required. This may require injector withdrawal, position correction or even continuing with the procedure without corrective actions taken based on the experience of the operator. Correlation between the detected injection force and the visual inspection of IOL 122 traveling inside transparent cartridge 120 allows the operator to judge the need of corrective actions under different scenarios. Detection of an increased force of injection will not always require aborting the injection process.

Figure 2:
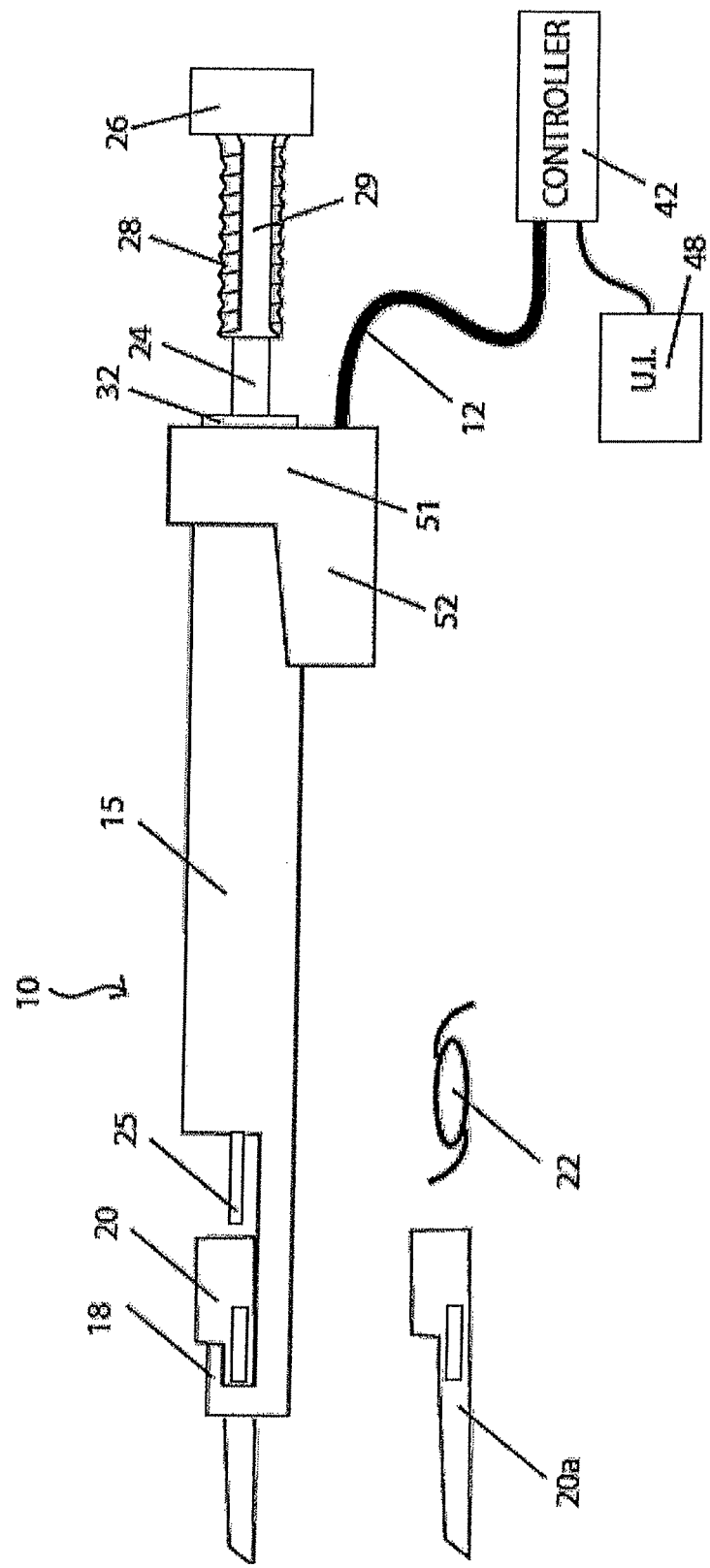
FIG. 2 is a side view of a dual mode IOL injection apparatus according to the principles of the present invention.

FIG. 2 is a side view of a dual mode IOL injection apparatus according to the principles of the present invention. IOL injection device 10 facilitates implanting an IOL 22 into a selected location of the eye. IOL injection device 10 includes a cable 12 that carries power and/or control signals from a separate controller module 42. Controller module 42 may include a user interface 48 and an input device such as a foot pedal, switch or other similar device (not shown). Some embodiments of the present invention may include in a main housing 15 one or more batteries to provide electrical power to the device and/or one or more switches or other user input devices and/or a controller to control the operation of the device.

The IOL injection device 10 also comprises a cartridge mount 18, which holds a removably mounted insertion cartridge 20 in a locked position. Cartridge 20 is also shown unmounted as 20a. Insertion cartridge 20 is typically a transparent disposable polymeric component adapted to accommodate an unfolded IOL and to fold and displace the IOL as the tip 25 of plunger 24 is translated forward from the body of housing 15 and through insertion cartridge 20. Tip 25 has a smooth surface that gently pushes IOL 22. In some embodiments, cartridge mount 18 may comprise a metallic "nosecone" that includes a unique cutout to accommodate the IOL cartridge and that is press-fitted to an inner shell of the housing 15. Some cartridges 20 may come with IOL 22 pre-loaded in unfolded position.

Plunger 24 is rotation restrained inside housing 15 and has a proximal portion including a male thread portion of threaded plunger shaft 28 and a rotating knob 26. An axially rotating joint (56 in FIG. 3) couples knob 26 and threaded plunger shaft 28 with plunger 24. One or more longitudinal zones of threaded plunger shaft 28 have been reduced to create a male key 29 matching with a complementary female key (37 in FIG. 3) in the center of a clutch disk 32. This mechanism is designed to allow axial displacement of threaded plunger shaft 28 across clutch disk 32 while producing rotational engagement between clutch disk 32 and threaded plunger shaft 28. In a preferred embodiment one or more flat areas disposed in a symmetrical manner conform to male key 29. Clutch disk 32 is rotated by a powered drive mechanism 51 enclosed within a drive mechanism housing 52. The powering portion of drive mechanism 51 can be detachably coupled to injector housing 15 in a way that injector 10 can operate manually as described in FIG. 1 when drive mechanism 51 is detached.

Figure 3:
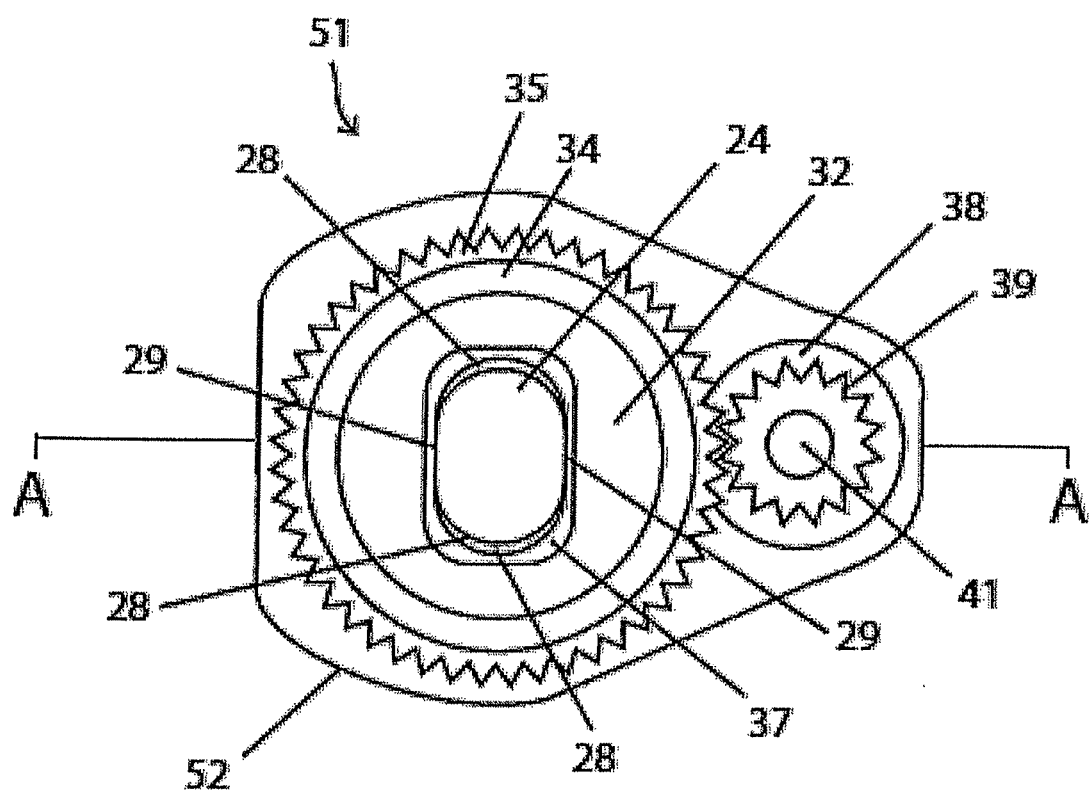
FIG. 3 is a schematic cross sectional view of a dual mode injector at the plane of the gear mechanism taken from B-B in FIG. 4.
Figure 4:
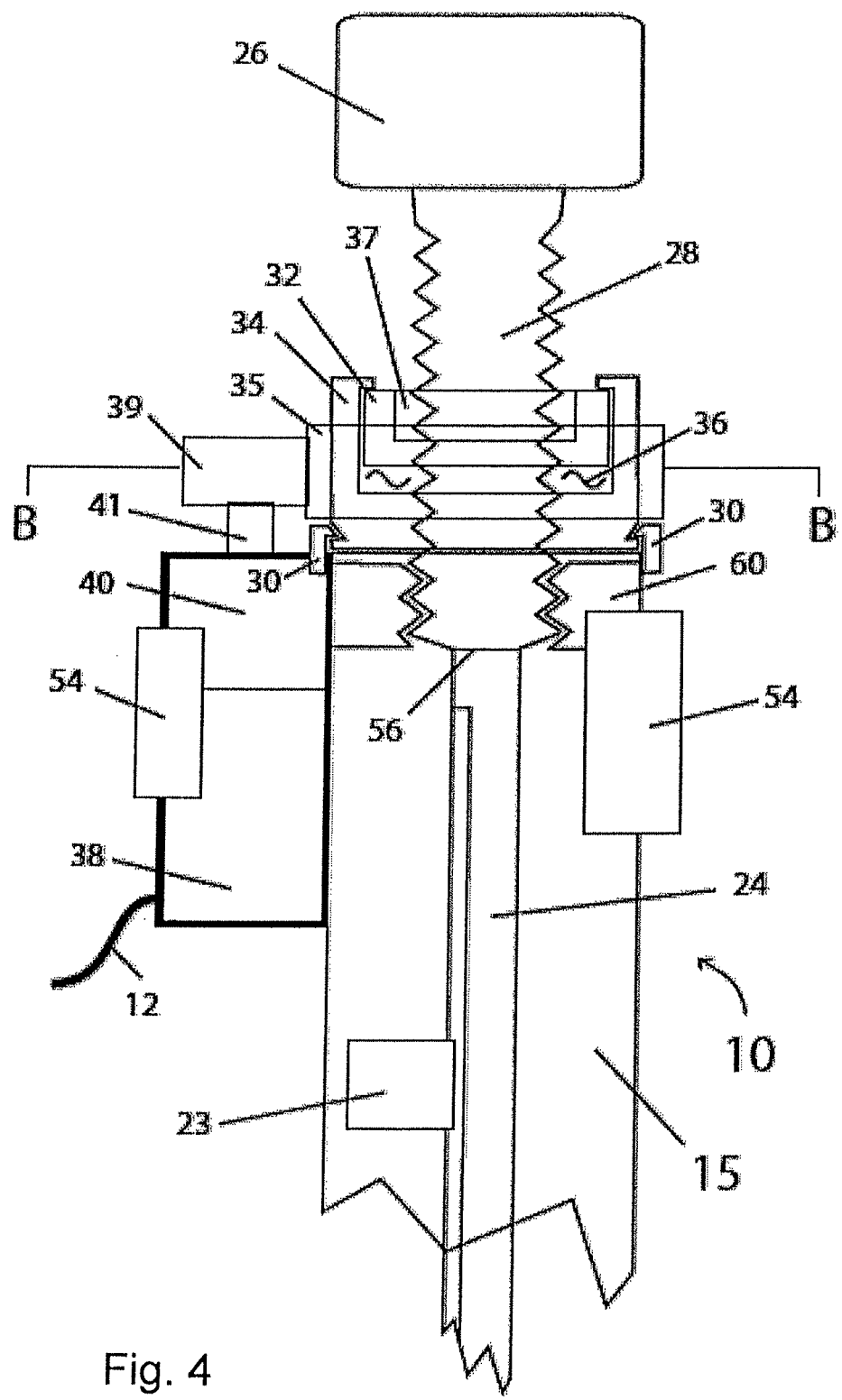
FIG. 4 is a lateral cross sectional view of the proximal portion of a dual mode injector taken from A-A in FIG. 3.

FIG. 3 is a schematic cross sectional view of a dual mode injector at the plane of the gear mechanism taken from B-B in FIG. 4. Motor 38 with an optional reduction gearbox 40 transmits rotational power through a shaft 41 to attached motor gear 39. A clutch drive disk 34 with attached drive disk gear 35 receives rotational power from motor 38. Drive disk holders 30 shown in FIG. 4 allow drive disk 34 to rotate coaxially with respect to injector housing 15. A normally engaged clutching mechanism is conformed between drive disk 34 and clutch disk 32, held in coaxial position by a rim of drive disk 34. A factory set compression force exists between disks 34 and 32 with an optional intermediate clutch lining 36, spring or other clutch coupling media. For example, clutch lining 36 can be complemented or replaced by a compressible washer or other equivalent clutch interface system providing a stable and predictable torque limiter capable of withstanding repeated sterilizations, moisture, debris, etc. Clutch disk center key hole 37 allows plunger 24 to be axially displaced freely and also to rotate freely because the reduced diameter of plunger 24. Threaded plunger shaft 28 with male key 29 can be freely displaced co-axially inside clutch disk key hole 37. Clutch disk 32 and threaded plunger shaft 28 are rotationally locked to each other by male key 29 and female key 37. Any suitable clutch mechanism can be employed to engage and disengage the motor power from the device 10. For example, in other embodiments of the present invention, instead of a mechanic clutch operating as a torque limiter, the same functionality can be incorporated using an electromagnetic clutch.

FIG. 4 is a lateral cross sectional view of the proximal portion of a dual mode injector taken from A-A in FIG. 3. Housing 15 has an internally fixated female thread 60 receiving plunger 24 in an axially unrestrained manner because of its reduced diameter. Plunger 24 is rotationally restrained by plunger rotation restrainer 23 engaging a slit or flattened segment along the main axis of plunger 24. Free axial displacement is possible when plunger 24 advances from a fully retracted position until threaded plunger shaft 28 engages with female thread 60. Free axial travel typically corresponds to the phases of cartridge insertion, IOL folding and advance into a pre-release position. From this point forward, axial displacement of plunger 24 is achieved by a clockwise rotation of knob 26 in which threaded plunger shaft 28 engages female thread 60. This portion of travel typically corresponds to IOL 22 delivery phase, where maximum control is required. When drive mechanism 51 is operationally attached by a fixation bracket 54, injector 20 can incorporate the powered mode of operation, overridable by manual operation in forward and reverse direction by disengagement of the torque limiter clutch mechanism.

To operate injector 10 an operator fully retracts plunger 24 by first counter rotating knob 26 until disengaging threaded plunger shaft 28 from female thread 60. This operation can be performed in powered mode by providing a plunger retract command into user interface 48, or in manual mode by grasping and turning knob 26 counterclockwise with a force enough to disengage the torque limiter clutch mechanism and rotate threaded plunger shaft 28 until released from female thread 60. At this point the operator performs the second step of fully retracting plunger 24 until it is in a rearward stop position. In this embodiment, this second step is always a manual procedure. With injector 10 having plunger 24 in a fully retracted position, the operator can insert an IOL loaded cartridge 22 into cartridge mount 18 in the locking position. Operator then manually advances plunger 24 by pushing and rotating knob 26 until threaded plunger shaft 28 with male key 29 travels across clutch disk 32 with female key 37 and threads threaded plunger shaft 28 minimally into female thread 60. During this action, plunger tip 25 folds and pushes IOL 22 distally into a pre-insertion position inside cartridge 20. At this point injector 10 is prepared for powered IOL injection.

After inserting the distal opening of cartridge 20 into a surgical incision in the eye, the operator provides an insertion command through user interface 48 to controller 42. Controller 42 provides power and control signals through cable 12 to produce forward actuation of motor 38. Controller 42 monitors the operation of motor 38 to detect proper operation and overload conditions. Relevant fault conditions such as motor malfunction or overload can be reported to the operator using user interface 48 to provide, for example, an audible or luminous warning signal. Motor rotational energy is transmitted through optional gearbox 40, and gear 39 to drive disc 34 which in turn transmits rotary power across the normally engaged clutch mechanism to clutch disk 32 with female key 37 acting as a torque limiter. When properly set, female key 37 has been manually engaged with male key 29 and threaded plunger shaft 28 has been minimally threaded into female thread 60. Following an operator command, drive mechanism 51 produces clockwise rotation of clutch disk 32 and threaded plunger shaft 28. Clockwise rotation of thread 60 by disk 32 produces forward displacement of plunger 24 as threaded plunger shaft 28 threads into female thread 60, controllably injecting IOL 22 into a selected position inside the eye. An operator can use a foot pedal or other input device from user interface 48 to command controller 42 to initiate lens injection, adjust plunger speed, accelerate, decelerate, stop and shift direction of operation. In this way, a high degree of control can be achieved during IOL injection.

In other embodiments, custom operation commands can be programmed into controller 42 according to operator preferences. Controller 42 can be programmed to deliver control signals to motor 38 that allow a non-uniform speed of operation. For example, motor speed can follow a ramp function progressively increasing motor speed after each activation cycle while resetting to low speed every time the system is restarted from the stop position for increased control. Other functions are possible. The operator can at any time stop or reverse the direction of plunger translation by providing the corresponding command using user interface 48. Plunger tip 25 travels into the eye being operated is physically limited in the same manner it is limited in manually operated IOL injectors of the prior art by reaching a fixed end-of-travel position determined by male thread length. At any time during powered operation, the operator can manually override powered operation simply by holding or rotating knob 26 in a desired direction. When holding knob 26 in a fixed position while clutch disk 32 is engaged and motor 38 is rotating, the torque limiter clutch mechanism disengages the translation of stopping plunger 24. Furthermore, regardless of motor activity, manual rotation of knob 26 in a clockwise direction with male and female threads 28 and 60 engaged produces forward translation of plunger 24, as the clutch mechanism is factory set to a torque release threshold level that always allows manual activation of injector 10 over powered activation of the injector 10. Similarly, manual counterclockwise rotation of knob 26 with an engaged threaded plunger shaft 28 will always produce rearward translation of plunger 24 regardless of the activity of drive mechanism 51.

Figure 5A:
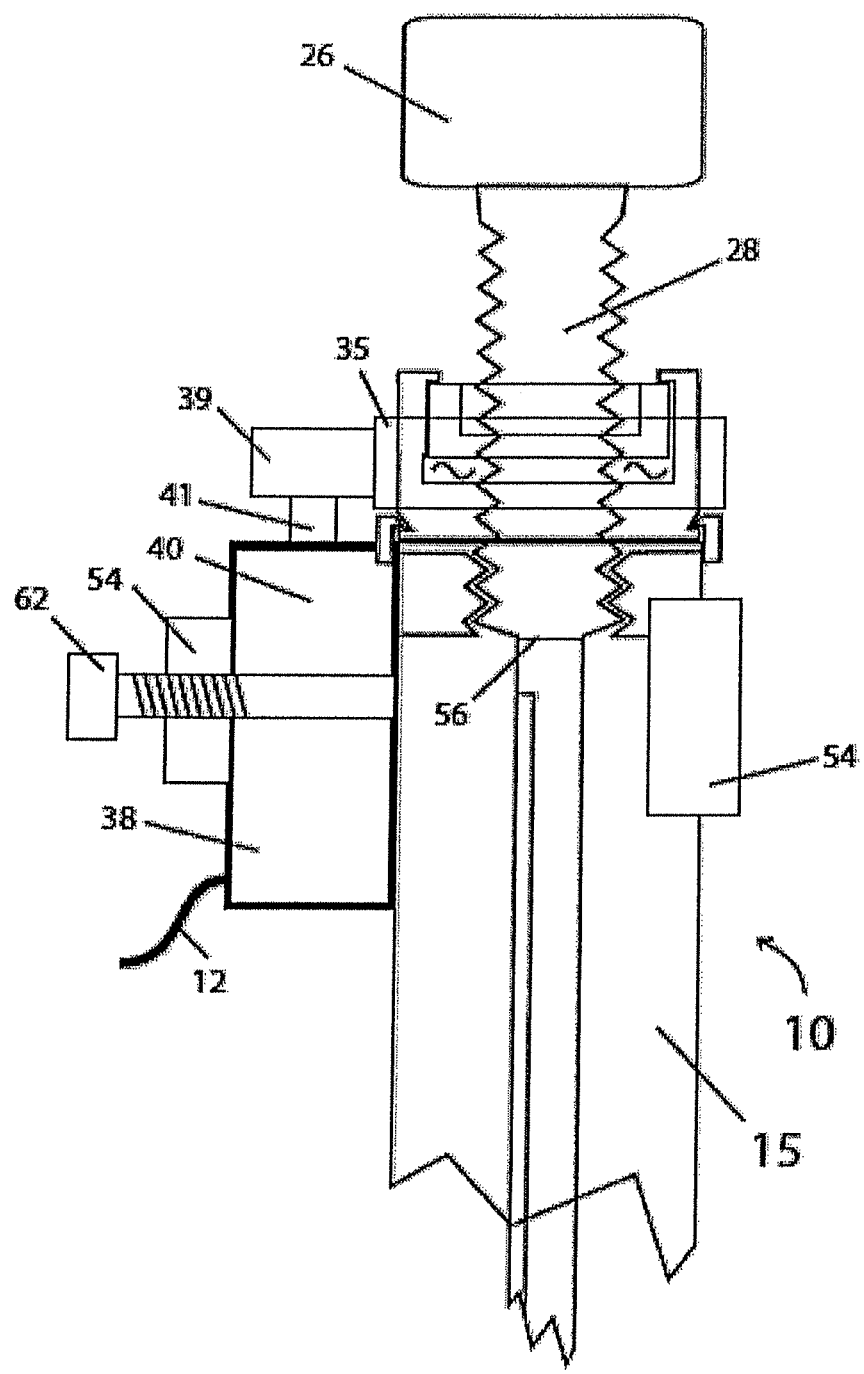
FIG. 5a and FIG. 5b are lateral cross sectional views of the proximal portion of a dual mode injector according to the principles of the present invention.
Figure 5B:
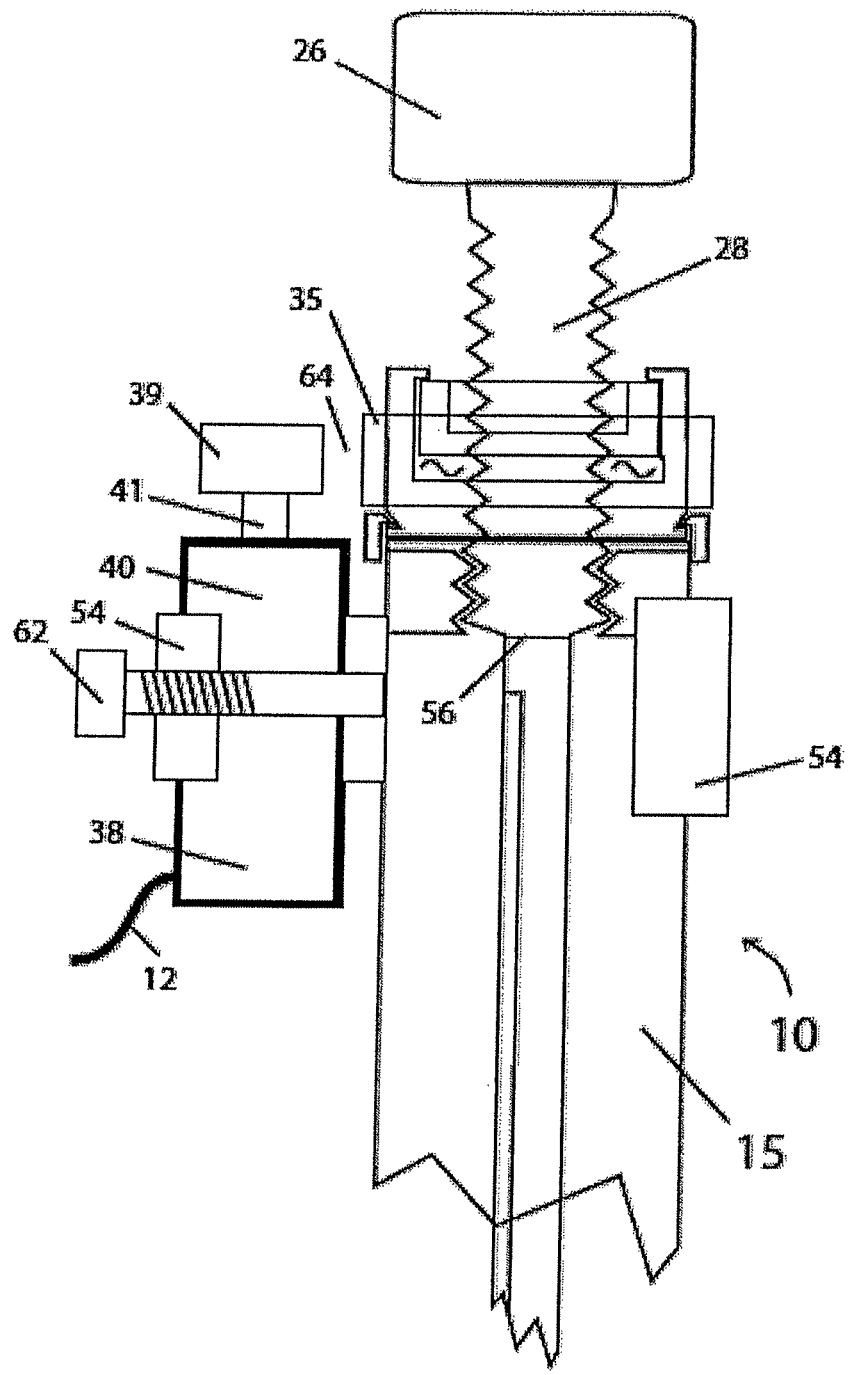

FIG. 5a and FIG. 5b are lateral cross sectional views of the proximal portion of a dual mode injector according to the principles of the present invention. This embodiment allows an operator to activate a knob with a screw 62 operational to separate or bring together gears 39 and 35. In one position, knob 62 puts gears 39 and 35 in functional contact engaging rotational power transmission between motor 38 and drive disk 34. In an alternative position, knob 62 is operational to separate gears 39 and 35 into a non-functional position introducing a gap 64 between gears. In this disengaged position, motor 38 has no loading effect and injector 10 can be manually operated through knob 26 providing optimal tactile feedback of resistance during plunger advance and retraction. Many other engage-disengage mechanisms are possible and the mechanism shown here is only for illustration purposes. Knob 62 can be designed to be operational for disengaging the drive system in one position and for full detachment of the drive system in another position, allowing the injector to be used in manual-only mode when the drive mechanism 51 is fully detached.

FIGS. 5a and 5b more clearly show the manual override feature of the present invention. In FIG. 5a, the drive motor is engaged, and the injector 10 is operated automatically by motor 38. In this configuration, motor 38 is coupled via optional gear box 40 and motor shaft 41 to drive gear 39. As motor 38 rotates so does motor gear 39. In this manner, motor 38 drives motor gear 39. If gearbox 40 is employed, then the gear ratio can be increased or decreased such that rotation of motor 38 is slower of faster (respectively) than rotation of motor gear 39. Typically, a gear box 40 is employed such that a faster rotation of motor 38 results in a slower rotation of motor gear 39 which allows for more precise control of IOL insertion through more precise control of the axial translation of plunger 24.

In FIG. 5a, motor gear 39 engages drive disk gear 35 which in turn engages the plunger threads on threaded plunger shaft 28. In this manner, motor gear 39 turns drive disk gear 35 which turns plunger 24. Because plunger threads on threaded plunger shaft 28 are engaged with female thread 60, as plunger 24 rotates, it also translates. In this manner, plunger 24 translates axially such that plunger tip 25 contacts the IOL and pushes it out of cartridge 20.

FIG. 5b shows the device 10 of the present invention in manual mode. In the configuration of FIG. 5b, motor gear 39 is disengaged from disk gear 35. In this case, operation of the device 10 is manual and is accomplished by turning plunger knob 26. In FIG. 5b, an engage-disengage screw 62 is turned so that the motor assembly is moved away from injector body 15. In this embodiment, engage-disengage screw 62 is coupled to fixation bracket 54.

In another embodiment of the present invention, a spring motor can be used as the drive mechanism 51 for injector 10. An attached or detachable winding lever common to spring motors is used to put the spring powered drive mechanism in a wound condition. A lever suitably positioned can be activated for plunger translation for lens injection. The system can be designed to operate only to inject, or for injection and retraction of the plunger. The same lever used for activation can be designed to indicate to the operator that the spring motor is properly wound for operation. Manual override is always available. An advantage of a spring motor powered IOL injector is wireless operation. Other motors such as pneumatic, piezoelectric, linear electric can be used as the drive mechanism 51 without departing from its scope.

FIG. 6 is a perspective view of a dual mode IOL injection device according to the principles of the present invention. In FIG. 6, plunger knob 26 is fixed to plunger 24 (not shown). Motor gear 39 is engaged with disk drive gear 35. Drive disc gear 35 is coupled to drive disc 34. Motor 38 is coupled to motor gear 39 via motor shaft 41 and optional gearbox 40 (not shown). Cable 12 provides power and control signals to motor 38. Drive mechanism 51 is at least partially enclosed by drive mechanism cover 52. Injector body 15 has a cartridge mount 18 and cartridge 20.

Figure 7:
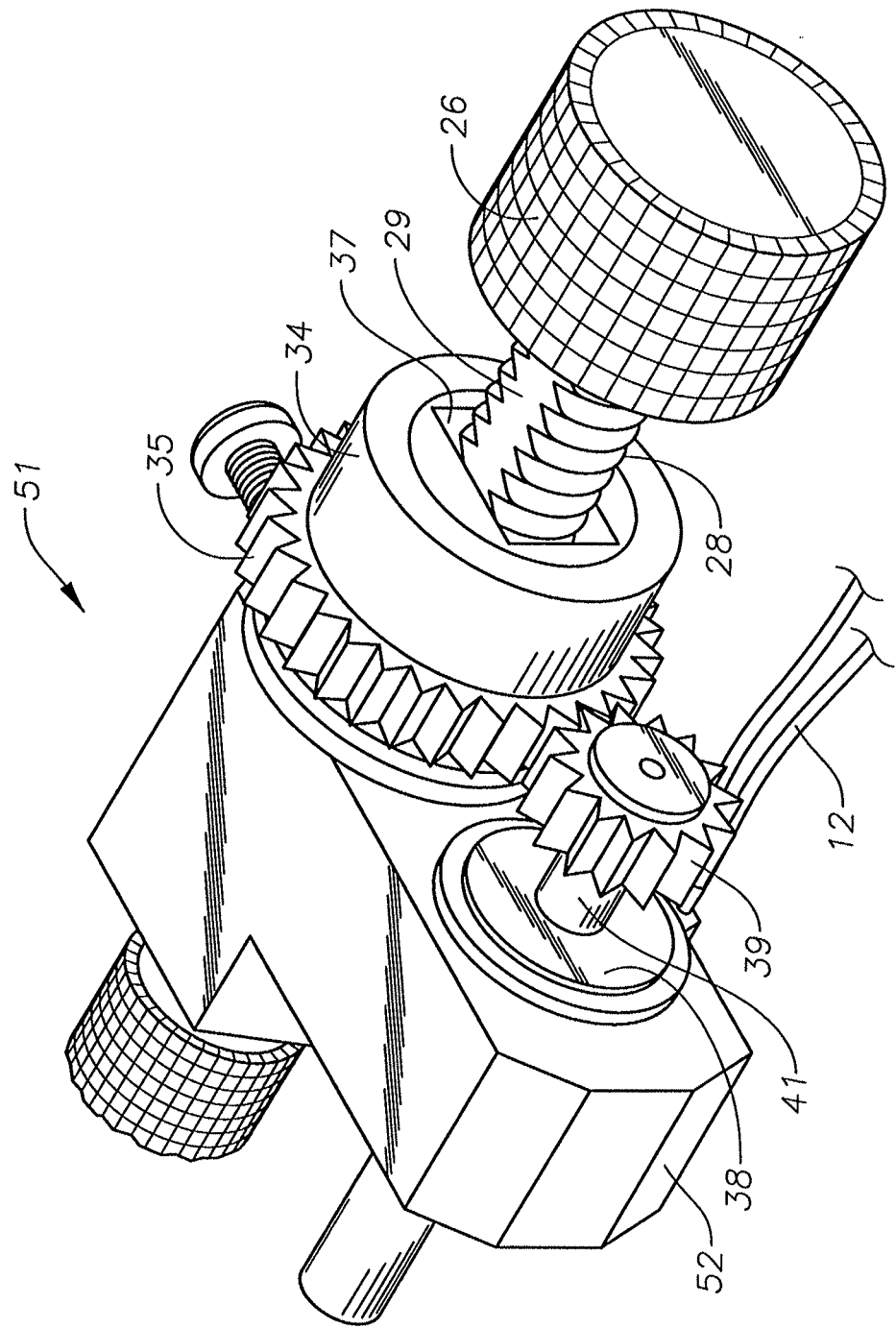
FIG. 7 is a perspective view of the proximal portion of a dual mode injector incorporating a clutch mechanism according to the principles of the present invention.

FIG. 7 is a perspective view of the proximal portion of a dual mode injector incorporating a clutch mechanism according to the principles of the present invention. In FIG. 7, plunger knob 26 is fixed to plunger 24 (not shown) via threaded plunger shaft 28. Threaded plunger shaft 28 has a male key 29 that acts as a key as previously described. Motor gear 39 is engaged with disk drive gear 35. Drive disc gear 35 is coupled to drive disc 34. Motor 38 is coupled to motor gear 39 via motor shaft 41 and optional gearbox 40 (not shown).

Cable 12 provides power and control signals to motor 38. Drive mechanism 51 is at least partially enclosed by drive mechanism cover 52.

Figure 8:
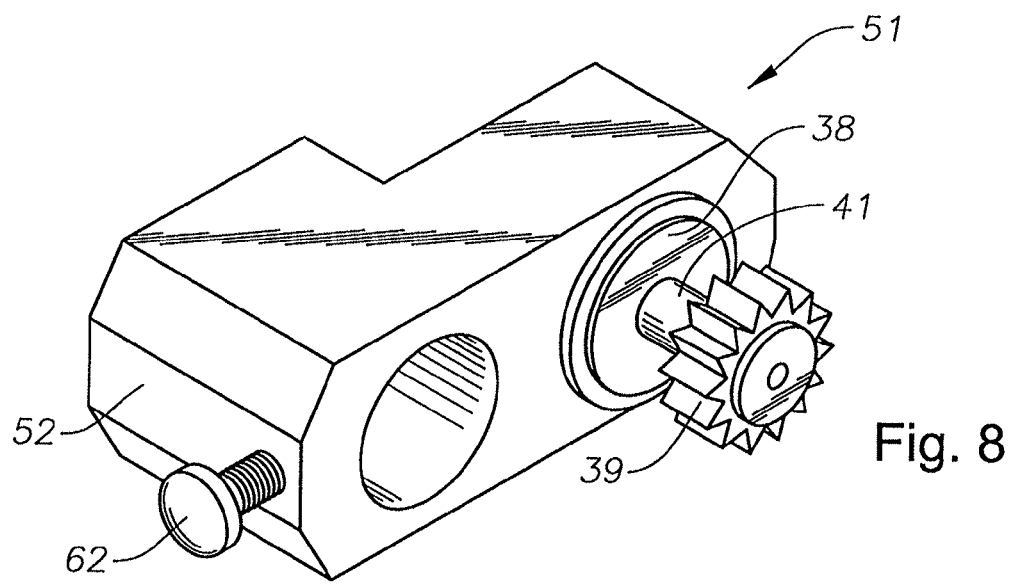
FIG. 8 is a perspective view of the powering portion of a dual mode injector including an electric micro-motor, reduction gearbox and gear according to the principles of the present invention.

FIG. 8 is a perspective view of the powering portion of a dual mode injector including an electric micro-motor, reduction gearbox and gear according to the principles of the present invention. Motor 38 is coupled to motor gear 39 via motor shaft 41 and optional gearbox 40. Engage-disengage screw 62 is threaded into fixation bracket 54. Engage-disengage screw 62 can contact housing 15 to hold the motor assembly in place on injection 10. Drive mechanism 51 is at least partially enclosed by drive mechanism cover 52.

FIG. 9 is a perspective view of a spring powered embodiment of a dual mode injector according to the principles of the present invention. Injector body 15 has a cartridge mount 18 and cartridge 20. Plunger knob 26 is fixed to plunger 24 (not shown) via threaded plunger shaft 28. Instead of a motor, a wound spring is used to provide the force to plunger 24 through the same gears previously described. In this manner, as the spring unwinds, it turns gears that cause plunger 24 to translate. The same clutch mechanisms previously described may also be used with the spring-driven embodiment of the present invention.

Figure 10:
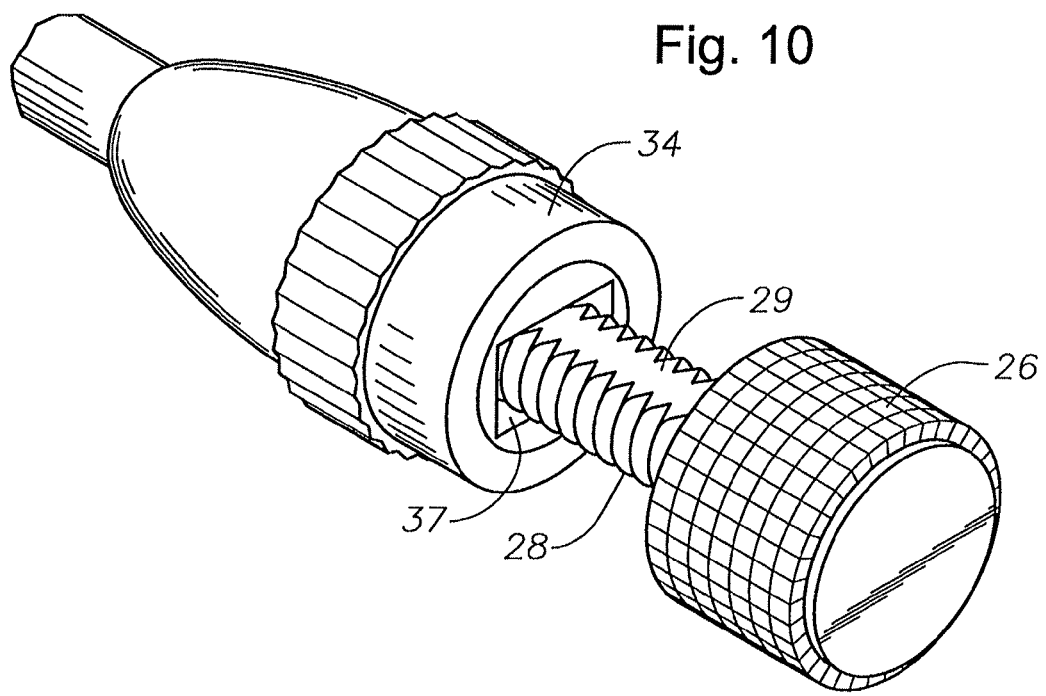
FIG. 10 is a perspective view of the powering portion of a dual mode injector including a spring powered mechanism according to the principles of the present invention.

FIG. 10 is a perspective view of the powering portion of a dual mode injector including a spring powered mechanism according to the principles of the present invention. Plunger knob 26 is fixed to plunger 24 (not shown) via threaded plunger shaft 28. Threaded plunger shaft 28 has a male key 29 that acts as a key as previously described. Instead of a motor, a wound spring is used to provide the force to plunger 24 through the same gears previously described. In this manner, as the spring unwinds, it turns gears that cause plunger 24 to translate. The same clutch mechanisms previously described may also be used with the spring-driven embodiment of the present invention.

From the above, it may be appreciated that the present invention provides an improved IOL injection device. The present invention provides an automated IOL injector with manual override capability. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An intraocular lens injector comprising:
a tubular housing having a primary axis extending between a front end and a rear end of the housing;
a plunger longitudinally disposed within the housing and having first and second ends, the first end being disposed towards the front end of the tubular housing, the plunger having a male key;
a drive system coupled to the housing, the drive system configured to cause longitudinal translation of the plunger along the primary axis of the housing, the drive system comprising a motor gear;
a normally engaged clutch system coupled to the drive system, the normally engaged clutch system allowing manual disengagement of the drive system, the normally engaged clutch system comprising a drive disk gear coupled to a clutch disk, the clutch disk having a female key, the male key of the plunger mateable with the female key of the clutch disk, the motor gear of the drive system engageable with the drive disk gear of the clutch system;
a knob coupled to the plunger, the knob allowing manual operation of the injector;
a cartridge mount near the front end of the housing, the cartridge mount configured to accommodate a removable insertion cartridge in alignment with the plunger so that an intraocular lens disposed in the insertion cartridge is displaced from the insertion cartridge as the plunger is translated towards the front end of the housing; and
an insertion cartridge removably mountable to the cartridge mount and adapted to accommodate the intraocular lens and to fold and displace the intraocular lens from the injector as the plunger is translated towards the front end of the housing.

2. The injector of claim 1 wherein the drive system comprises a motor selected from the group consisting of: electric motor, brushless motor, stepper motor, piezoelectric motor, linear motor, spring motor, and pneumatic motor.

3. The injector of claim 1 further comprising:
a control system responsive to user input, the control system configured to cause the drive system to translate the plunger.

4. The injector of claim 1 wherein the normally engaged clutch system is operative as a torque limiter.

5. The injector of claim 4 wherein the torque limiter is selected from the group consisting of: a mechanical clutch and an electromagnetic clutch.

6. The injector of claim 4 wherein the clutch system automatically disengages when a preset torque limit is reached.

7. The injector of claim 1 wherein the drive system is engageable and disengageable from the plunger.

8. The injector of claim 7 wherein the injector is operational in manual mode while the drive system is disengaged from the plunger.

9. The injector of claim 1 wherein the drive system is detachably coupled to the tubular housing.

10. The injector of claim 1 wherein manual operation of the injector can be selected by a user to override the drive system.

11. The injector of claim 1 wherein the drive system further comprises:
an overrunning clutch mechanism configured to provide resistance feedback to an operator during manual operation.

12. The injector of claim 1 wherein the injector is operational in manual mode while the drive system is operable.

13. The injector of claim 1 wherein the drive system is capable of operating at non-constant speed.

14. The injector of claim 1 further comprising:
a removable plunger tip configured to snap fit on the first end of the plunger so that the removable plunger tip engages an intraocular lens as the plunger is translated towards the front end of the housing.

* * * * *